United States Patent [19]

Elliott

[11] Patent Number: 5,071,414
[45] Date of Patent: Dec. 10, 1991

[54] PACKAGING POCKET FOR DISPOSABLE DIAPER

[76] Inventor: Donald P. Elliott, 4200 W. Conejos Pl., Denver, Colo. 80204

[21] Appl. No.: 441,532

[22] Filed: Nov. 27, 1989

[51] Int. Cl.$^5$ .............................................. A61F 13/15
[52] U.S. Cl. .................................. 604/385.1; 604/358
[58] Field of Search ............................ 604/385.1, 358

[56] References Cited

U.S. PATENT DOCUMENTS

| | | | |
|---|---|---|---|
| 3,604,423 | 9/1971 | Fraser | 604/385.1 |
| 3,731,689 | 5/1973 | Schaar | 604/385.1 |
| 3,865,110 | 2/1975 | Traverse | 604/385.1 |
| 3,963,029 | 6/1976 | Brooks | 604/385.1 |
| 4,085,753 | 4/1978 | Gellert | 604/385.1 |

Primary Examiner—Randy Citrin Shay
Assistant Examiner—G. Gueltieri
Attorney, Agent, or Firm—Richard W. Hanes

[57] ABSTRACT

An improvement to a disposable diaper, forming a self packaging pocket integral with one of the body panels of the diaper and comprising a pliant membrane disposed and secured to the outside moisture impervious backing surface of the diaper body over the end area thereof and forming a transverse open ended pocket to be turned inside out over the rolled up diaper after its use to seal and compactly store the used diaper in a rolled up configuration.

1 Claim, 2 Drawing Sheets

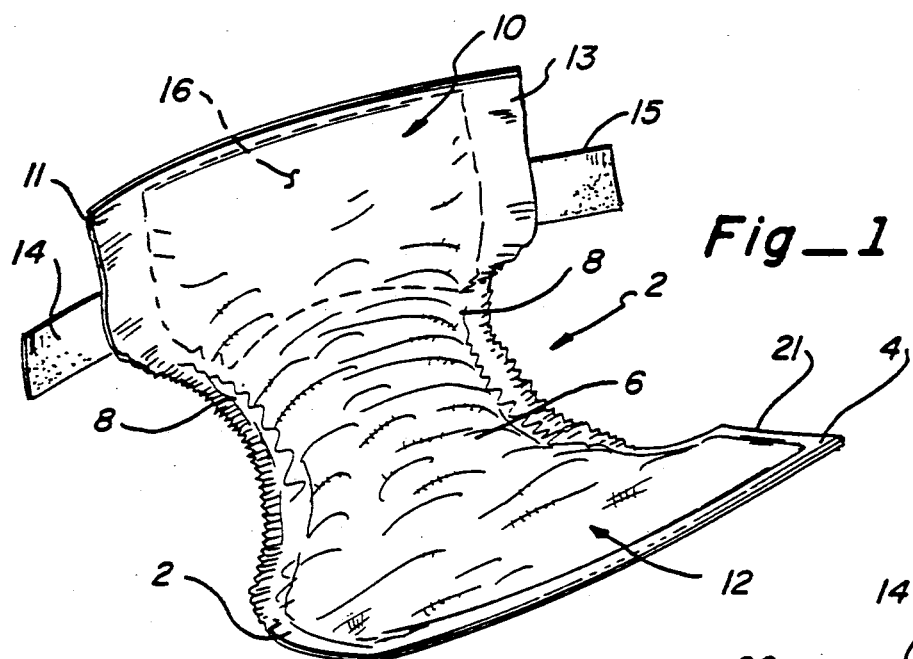
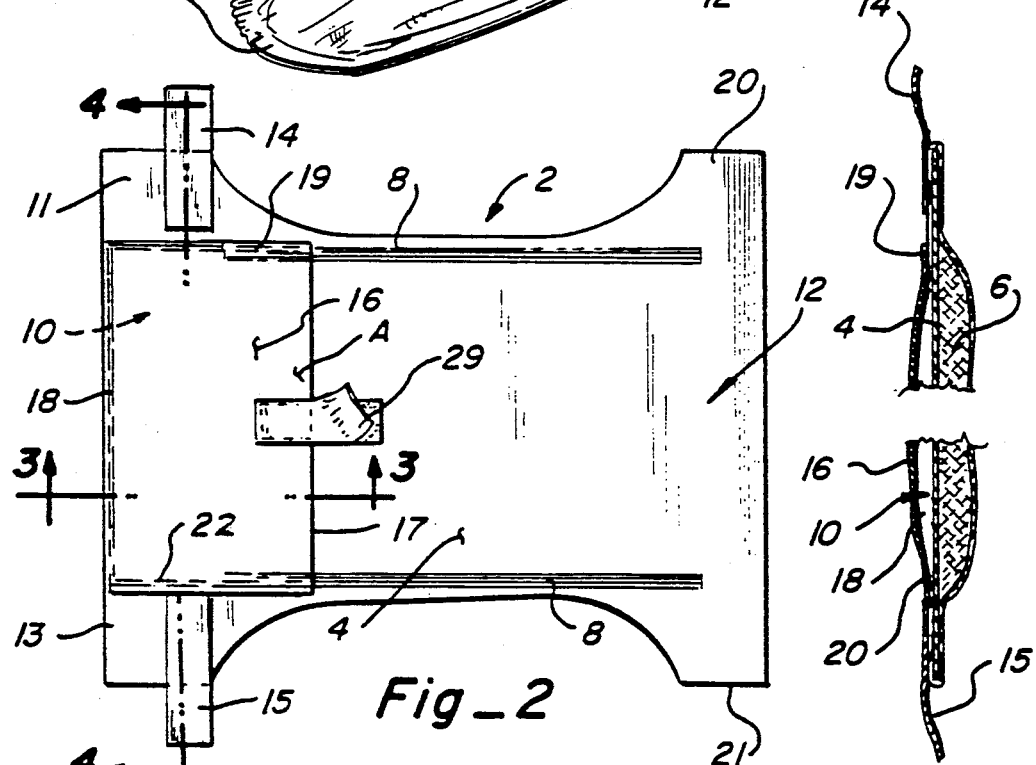
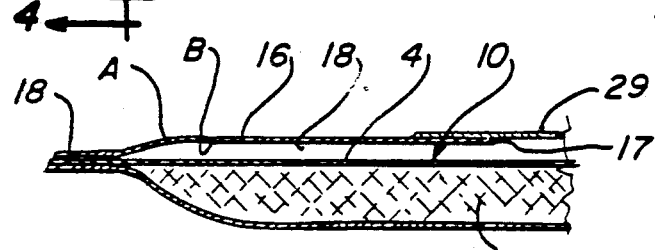

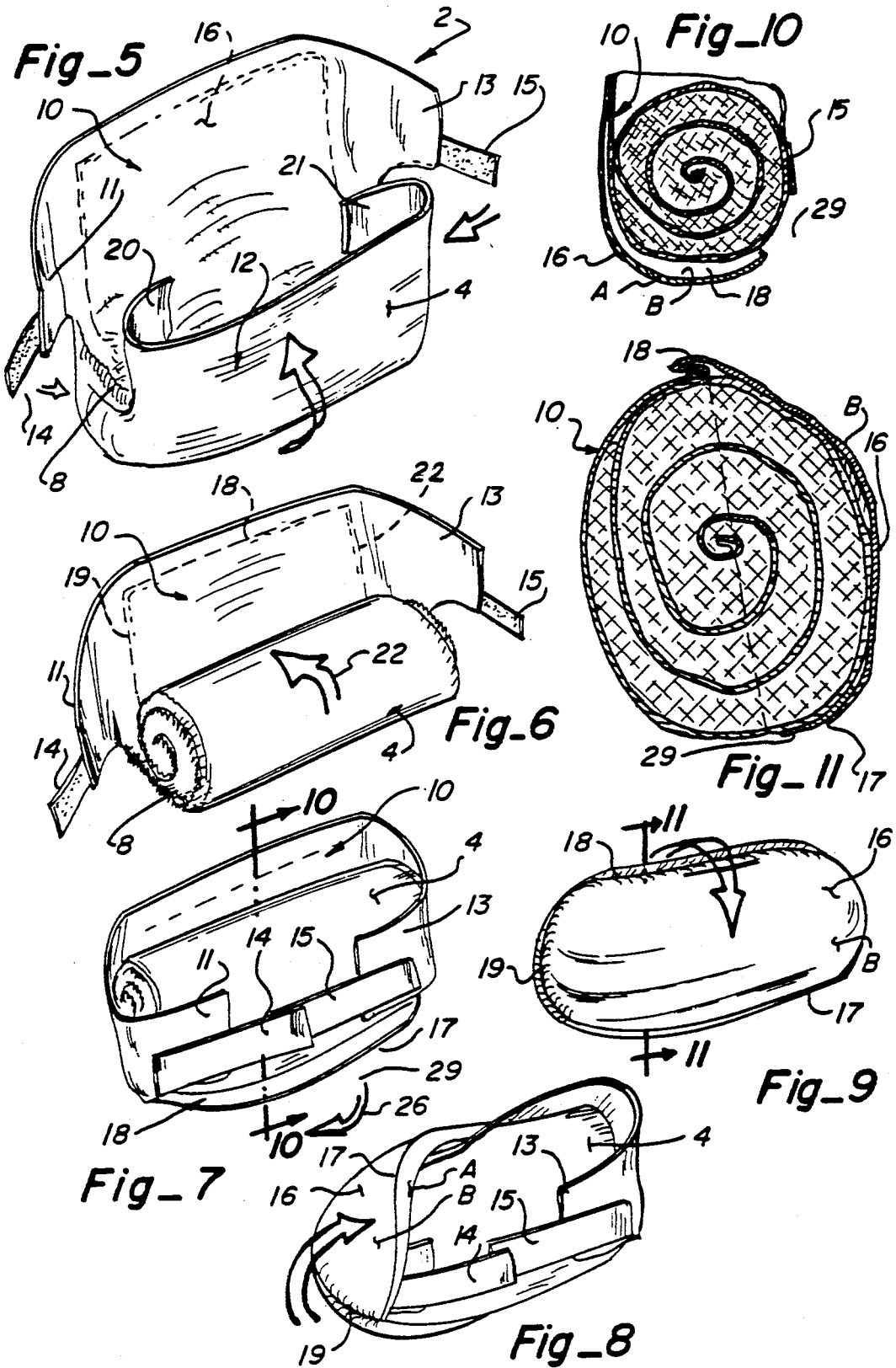

PACKAGING POCKET FOR DISPOSABLE DIAPER

BACKGROUND OF THE INVENTION

The present invention relates to diapers and specifically to an integral pocket in a disposable diaper which provides a means for rolling and packaging the diaper after use for easy and convenient compact disposal.

Disposable diapers have been popular as replacements for the traditional cloth diapers for many years. Although these products are expendable and are said to be disposable they are clumsy, inconvenient and untidy to throw away because a rolled up, used diaper tends to unroll and become awkwardly bulky and offensive.

Packaging a rolled cloth item in a pocket formed by turning a portion of the item inside out upon itself has been done with various items of clothing, such as a rolled pair of socks, but the use of that concept has not been made possible with a disposal diaper because the necessary structural elements to make it work are not present. The closest approach to a solution is found in U.S. Pat. No. 3,877,432 and U.S. Pat. No. 4,085,753. Some similarity of purpose is also seen in U.S. Pat. No. 3,369,545 and U.S. Pat. No. 4,803,175.

As the description of the present invention progresses, it will be seen that the construction of this invention has several significant and practically useful features which improve on the disposal bag of U.S. Pat. No. 4,085,753 and similar structures. First, the '753 bag requires a backsheet construction of two plies of material, whereas the instant structure requires only one sheet of material placed in juxtaposition to the diaper panel itself. Second, and most importantly, the '753 structure cannot be rolled up, as is customary with the disposal of such diapers, but must, on the other hand, be pried loose from the plies of material forming the bag and then folded once and pulled through the bag from the bottom, all of which is awkward, time-consuming and, most of all, ineffective to cleanly and efficiently dispose of the diaper in a tidy fashion.

With respect to the diaper disclosed in U.S. Pat. No. 3,369,545, it is difficult to ascertain exactly how the inventor intends to dispose of the diaper. The pouch of that diaper is said to be of such dimension with respect to the absorbent that upon reversal it can contain the entire soiled diaper. The instant diaper, however, is designed to be rolled up and then contained by a integral pocket, a process which is easily performed when the pocket is outside of the impervious sheeting which shields the pocket from the soiled or wet absorbent material. The primary disadvantage of the '545 structure is that the manipulation of the diaper during the reversal process brings the wet absorbent material into direct contact with the hands of the person handling the diaper. With the improved construction of the present invention, the diaper may be rolled and disposed of without any contact with the absorbent material. The so-called process of reversal is shown in FIG. 6 of the '545 patent and manifests the same disadvantages as the device of the '753 patent.

The provision of the pocket of the present invention to disposable diapers, however, is not the mere new use of an old concept or devise. It is apparent that the disposable diaper industry has progressed for many years with new and improved absorbent materials, elastic bands integrated into the plastic backing material and adhesive fastening bands which make application and removal of a diaper quick and easy. However, in spite of compelling need, disposable diapers become disposal problems after they have been used.

It is therefore the primary object of the present invention to provide an integral means for enabling the rolling up and packaging of a used diaper so as to reduce the bulk of the item, seal in odors and prevent the diaper from inelegantly unrolling.

A second object of the invention is to provide an integral pocket for disposal of diapers that significantly improves on the overall effectiveness of prior art devices of the same general type.

A third objective of the invention is to provide a diaper throw-away package that does not require the use of special sealing and fastening means for sealing and integration.

THE DRAWINGS

The present invention is illustrated by the accompanying drawings in which:

FIG. 1 is a perspective view of the inside surface of a typical disposable diaper.

FIG. 2 is an underside plan view of the diaper of the present invention.

FIG. 3 is an enlarged cross-sectional view of the diaper of the present invention taken along lines 3—3 of FIG. 2.

FIG. 4 is a fragmentary cross-sectional view of the diaper of the present invention taken along lines 4—4 of FIG. 2.

FIG. 5 is a perspective view from front to rear.

FIG. 6 is a perspective view of the diaper shown in FIG. 5 but shown in the process of being rolled.

FIG. 7 is a perspective view of the diaper in rolled-up configuration with the open edge of the inventive pocket shown at the bottom of the roll prior to its being turned inside out over the top of the roll.

FIG. 8 is a perspective view similar to FIG. 7 wherein the inventive pocket has been turned inside out and the pocket forming sheet is half-way turned back upon the roll to partially envelop it.

FIG. 9 is a perspective view similar to that of FIG. 8, but showing the pocket forming sheet having been completely pulled down over the rolled diaper to fully envelop and package the same.

FIG. 10 is a cross-sectional view taken along lines 10—10 of FIG. 7.

FIG. 11 is a cross-sectional view taken along lines 11—11 of FIG. 9.

DETAILED DESCRIPTION OF INVENTION

Referring first to FIG. 1, a disposable diaper is generally illustrated and referred to by reference numeral 2. The diaper comprises a plastic, moisture-impervious backing 4 onto which is attached one or more layers of absorbent material 6. Elastic bands 8 are sewn into the concave shaped sides of the diaper crotch portion in order to secure the same tightly around the legs of the wearer (not shown). Front and rear panels, 12 and 10 respectively, are extensions of the crotch-embracing material of the diaper and together form a waist band to hold the diaper in place. Adhesive strips 14 and 15 are attached to the laterally extending ears 11 and 13 of the rear panel 10 so as to be fastened to tabs 20 and 21 laterally extending from the sides of the rear panel 10, in order to form leg holes, the perimeters of which are bounded by the two elastic bands 8.

As particularly illustrated in FIGS. 2, 3 and 4, the pocket of the present invention comprises the conventional diaper-backing material 4 and a pliant membrane or sheet 16 having outside and inside surfaces A and B respectively, and being substantially rectangular in shape and sewn or otherwise attached along its base and two of its sides to the outside of the rear panel 10 of the diaper. The base line 18 of the sheet 16 is attached to the "top" edge of the panel 10. The two sides of the sheet 16 are attached to the diaper body along lines 19 and 22 which are substantially in alignment with the elastic bands 8. The attachment of the pliant sheet 16 to the diaper body forms a pocket 18 between the sheet 16 and the rear panel backing member 4. An adhesive fastening strip 29 may be placed on the outside surface A of the pocket sheet 16 perpendicularly to the unfastened open edge 17 of the membrane 16 to further secure the package, as will be explained in connection with a later description of how the pocket operates to form the disposable diaper package. The strip 29 is, however, unnecessary to the formation of a tightly compacted and secure package.

The operation of the packaging pocket of the diaper may be understood by referring to FIGS. 5 through 11. FIG. 5 shows a typical disposable diaper immediately after removal from the wearer. The front panel tabs 20 and 21 are folded inwardly out of the way and the diaper is rolled, beginning with the front panel 12, in the manner shown in FIG. 6 by the large directional arrow 22.

The adhesive strips 14 and 15 may be secured to each other or to the exposed backing material 4, as shown in FIG. 7, if they are still adhesive and usable, but the use of the adhesive strips is not necessary to the accomplishment of the packaging taught by this invention. The ears 11 and 13 and the strips 14 and 15 may be folded inwardly upon the inside surface of the panel 10 and thus become part of the roll, similarly to the way in which the tabs 20 and 21 were dealt with.

From the rolled up configuration shown in FIG. 7, the use of the inventive pocket of the present invention is initiated. The front facing open edge 17 of the pliant sheet 16 is pulled backwards in the direction shown by the large arrow 26, turning the pocket 18 inside out. The front edge 17 is brought around from behind the rolled up diaper mass and pulled down over its exposed frontal area, as shown in FIG. 8. FIG. 9 illustrates the pliant pocket facing sheet 16 having been completely everted to enfold the rolled diaper, compressing the resultant package for efficient storage and disposal, and preventing it from unrolling. The resultant roll is so compact as to effectively seal the package against escaping moisture and odor. Note that surface B of the sheet 16, which was, at the beginning of the process, the inside surface of the pocket, is now, in FIGS. 8 and 9, the outside surface of the roll. If the adhesive strip 29 is included as part of the pliant membrane 16, the adhesive surface of the strip may be fastened to the exposed backing material 4 to further secure the package.

I claim:
1. In a disposable diaper having,
   inside absorbent crotch means carried by a moisture impervious outside backing means comprising,
   front and back body panels the opposing ends of which have edges which form a waist band,
   securing means for securing said diaper in a closed position for wear attached to one of said panels, the improvement comprising,
   a pliant membrane member secured to and covering that portion of the impervious outside backing means which forms said one panel to which said securing means is attached, said membrane member forming an open ended pocket between said one panel and said pliant membrane member, wherein the open end thereof faces the other panel.

* * * * *